(12) United States Patent
Lee

(10) Patent No.: US 8,202,487 B2
(45) Date of Patent: *Jun. 19, 2012

(54) MULTIPLE ANALYTE ASSAY DEVICES

(76) Inventor: Jin Po Lee, Carlsbad, CA (US)

( * ) Notice: Subject to any disclaimer, the term of this patent is extended or adjusted under 35 U.S.C. 154(b) by 1557 days.

This patent is subject to a terminal disclaimer.

(21) Appl. No.: 11/401,193

(22) Filed: Apr. 10, 2006

(65) Prior Publication Data

US 2006/0193746 A1 Aug. 31, 2006

Related U.S. Application Data

(63) Continuation-in-part of application No. 10/019,570, filed as application No. PCT/US98/15369 on Jul. 22, 1998, now Pat. No. 7,347,972.

(51) Int. Cl.
*G01N 33/48* (2006.01)

(52) U.S. Cl. ........ 422/401; 422/420; 422/430; 436/164; 436/165

(58) Field of Classification Search .......... 422/401, 422/420, 430; 436/164, 165
See application file for complete search history.

(56) References Cited

U.S. PATENT DOCUMENTS

| 4,056,359 A | 11/1977 | Janin |
| 4,518,565 A | 5/1985 | Boger et al. |
| 5,403,551 A | 4/1995 | Galloway et al. |
| 5,770,458 A | 6/1998 | Klimov et al. |
| 5,976,895 A | 11/1999 | Cipkowski |
| 6,379,620 B1 * | 4/2002 | Tydings et al. ................ 422/58 |
| 6,514,769 B2 | 2/2003 | Lee |
| 6,548,019 B1 * | 4/2003 | Lee et al. ................ 422/58 |
| 6,730,268 B2 * | 5/2004 | Lee et al. ................ 422/58 |
| 7,347,972 B1 * | 3/2008 | Lee ................ 422/58 |

FOREIGN PATENT DOCUMENTS

DE 297 02 825 U1 5/1994

* cited by examiner

*Primary Examiner* — Lyle Alexander
(74) *Attorney, Agent, or Firm* — Bernd W. Sandt

(57) ABSTRACT

An assay device allowing for the testing for multiple analytes in a liquid sample simultaneously by employing a multiplicity of analyte testing strips which protrude from a housing containing slots for each assay test strip and wherein the flow of sample of the test strip is controlled by a cover over the sample contact pad which is inserted into the sample.

6 Claims, 3 Drawing Sheets

MULTIPLE ANALYTE ASSAY DEVICES

BACKGROUND

This application is a continuation in part of U.S. patent application Ser. No. 10/019,570 filed Nov. 8, 2001, now U.S. Pat. No. 7,347,972 which is based on PCT application US98/15369 filed Jul. 22, 1998.

FIELD OF INVENTION

The present invention relates to methods and devices for assaying biological fluid samples. More particularly the invention relates to assay methods and devices for detecting analytes, such as drugs, in urine.

HISTORY OF RELATED ART

In their most simple form, chromatographic analyte devices permit an assay to be performed in a single step application of an analyte sample to the device to produce visually observable assay results (such as those indicated by colored bars on the test strip contained in the device). However a common limitation of such devices is that they can only be used to detect a single analyte, requiring that serial assay procedures be performed to detect additional analytes. Multiple dipping steps such as are commonly used when multiple dipstick assays are separately performed, present not only possible loss of sensitivity of the assay (through reagent mixing or possible loss reagent solutions) but also an esthetic and hygienic problem for the analyst. Repetitive performance of assay procedures is also tedious, which increases the risk that assays will be performed improperly or the results misinterpreted.

SUMMARY OF THE INVENTION

The present invention provides an assay device and methods for performing multiple analyte assays. In one embodiment of the assay device, the device is a dipstick having multiple test strips, each of which includes means for absorbing a controlled amount of sample to conduct the test, a test zone and a control zone. The test strips are partially enclosed in a housing having an open side through which a protected end of each test strip protrudes. The protruding end contains the means to absorb the sample when contacted with the analyte and also is protected by a cover which limits and controls the absorption of a liquid sample to prevent flooding of the test strip in the channels of the housing. A protective cap is provided to further seal the protruding ends of the strips from exposure while not in use. Each test strip is separated from the next within the housing by raised spacers. The portion of the housing, which overlies the test and control zones, is transparent to permit visually observable results shown in each zone to be viewed.

In cassette form, the assay devise has the same structure described above, but the protruding test strips are inserted into a cap, which has a sample port for application of sample to the test strips. The cap is retained on the assay device by a close fit over the device housing.

Each test strip provides binders and assay reagents for detection of a different analyte in the sample field. In a particularly preferred embodiment of the assay device, the housing may be opened to permit substitution of different test strips to allow each device to be customized for detection of specific analytes of interest. Each test strip further contains a separate cover over the protruding end that contains the sample pad. The cover protects the sample pad and hence the strip from contamination and also limits the flow of the sample to the assay strip so as to prevent flooding of the sample.

The assay device of the invention makes specimen analysis easier and increases its accuracy because an analyte sample need only to be applied once to the assay device for testing and can, in the same step, be evaluated for potential adulteration or compromise. In addition, the replaceable nature of the analyte test strips allows the analyst to customize the array of assays to the testing situation. Because the customization can be performed before adding the test sample (e.g., urine), fewer manipulations with the analyte sample are needed to obtain the desired information. In addition, use of the separator device permits further testing of the sample to be performed without risk of adulterating the sample in a preliminary assay performed according to the invention.

The invention also provides a method for assaying one or more analytes of interest using one or more assay strips. The protruding ends of the device are dipped into a fluid analyte sample. Binding of an analyte present in the sample with one or more specific ligands causes formation of specific visual pattern in the test and control zones indicative of the test result.

The assay results obtained according to the invention may be read visually without use of separate measuring equipment. Thus, performance of assays according to the invention requires only that the user introduce the requisite amount of test sample into the device of the invention, then observe any color changes which appear shortly thereafter in a detection zone of an analyte strip. The method of the invention is especially useful for screening fluid analyte samples (e.g., urine) for the presence or absence of drugs of abuse.

DETAILED DESCRIPTION OF INVENTION

A. Definitions

Figure 1:
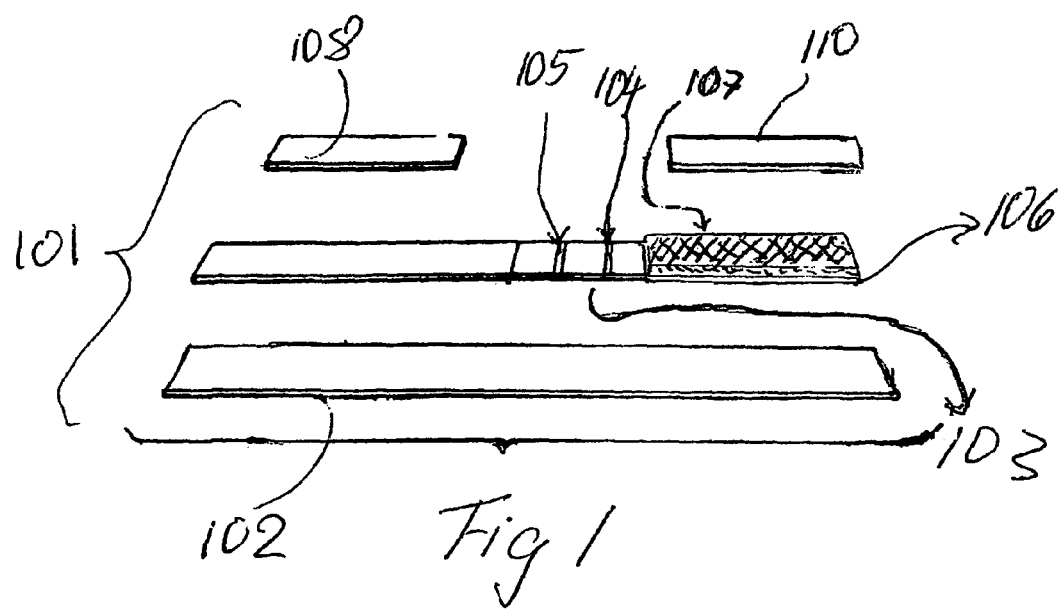
FIG. 1 is an exploded view of the assay strip used in the assay device of the invention

For ease of understanding, the following definitions will apply throughout this description:

1. The term "antigen" as used herein refers to any analyte, which is capable of binding antibodies. Antigens may comprise, without limitation, chemical compounds, polypeptides, carbohydrates, nucleic acids, lipids, and the like, including viral particles, viral subunits, bacterial and parasite surface antigens, and host proteins that may be diagnostic of the subject's condition.

2. A "binder" refers to a ligand for the analyte as in the format of a sandwich assay, or a ligand for both the analyte and the tracer as in the format of a competitive assay. A binder can be chosen from a group of molecules or compounds capable of binding the analyte, such as an antigen to the antibody analyte, or an antibody to the antigen analyte.

3. A "test zone" refers to an area in which a binder or the analyte is attached, movably or immovably, to the analyte test strip portion of an assay device.

4. A "tracer" refers to a ligand for the analyte or the binder labeled with a detectable label, preferably a visually readable particulate label, such as colloidal gold, latex and liposomes including dye, carbon black, and the like.

5. A "sample loading zone" refers to an area of a analyte test strip on which a fluid, generally a liquid, analyte sample is applied for migration to the test zone.
6. A "analyte test strip" of the invention consists of, collectively, all of the zone supporting membranes and any filters of the assay device.
7. A "fluid analyte sample" can be any fluid suspected of containing analyte of interest for which a particular assay is specific. Test sample may represent any body fluid, including urine, blood, sweat, lymph, intraperitoneal fluid, crude tissue extract or homogenate, derived from a fetus, neonate, juvenile or adult subject; a non-biological fluid such as water from some ecological niche, e.g., a river or a lake; or a solution used in a laboratory.
8. A "label" is a molecule or compound, which directly or indirectly mediates the formation of a signal (such as a color change), which is used in assay to indicate the presence, absence or concentration range of analyte of interest in a test sample. Labels may include enzymes, fluorescers, liposomes, erythrocyte ghosts, polymer microcapsules, color polymer particles (latex), and preferably includes sols of metal-containing compounds. A wide variety of patents and patent applications provide an extensive literature of different techniques for producing detectible signals in immunoassays. The following list of United States patents is merely illustrative of the type of label which can find application in this invention: U.S. Pat. No. 3,646,346 discloses radioactive label; U.S. Pat. Nos. 3,654,090, 3,791,932, and 3,817,838 disclose enzyme labels; U.S. Pat. No. 3,996,345 discloses fluorescer-quencher labels; U.S. Pat. No. 4,062,733 discloses radioactive label; U.S. Pat. No. 4,067,959 discloses fluorescer or enzyme label; U.S. Pat. No. 4,104,099 discloses chemiluminescent label; and U.S. Pat. No. 4,160,645 discloses non-enzymatic catalyst label. U.S. Pat. No. 3,966,879 discloses an electrophoretic technique employing an antibody zone and U.S. Pat. No. 4,120,945 discloses a radioimmune assay (RIA) where labeled analyte is initially bound to a solid support through antibody. U.S. Pat. No. 4,233,402 discloses enzyme pair labels; U.S. Pat. No. 4,720,450 discloses chemically induced fluorescent labels; and U.S. Pat. No. 4,287,300 discloses enzyme anionic charge labels.

Labels can also be metal-containing sols; i.e., metal or metal compounds such as metal oxides, metal hydroxides, metal salts, metals or metal-containing compounds mixed with polymers or coated onto polymer nuclei. These metal labels may include dry forms of any of the above-named metal or metal compound sols, and preferably includes colloidal gold in dry form 9. A "complex" means (depending on the context) any multimolecular complex formed by analyte and one or more ligands, or by labeled ligand and immobilized ligand. In a sandwich-type immunoassay, e.g., the following complexes occur: analyte/labeled ligand duplex first produced in the assay (first complex) and analyte/labeled ligand/immobilized ligand triplex formed second in the assay (second complex).
10. "Fluid communication" refers to structures, which are in contact with, but not necessarily affixed to, one another.
11. "Assay" refers to several different types of assay formats in which an analyte of interest can be detected using an assay analyte test strip. For example, in a sandwich-type immunoassay, analytes of interest in the analyte sample, when present, bind a labeled tracer movably incorporated in the analyte test strip (consisting of a porous membrane) at the tracer zone to form a first complex. The tracer is a molecule which binds the analyte of interest and is conjugated to a label, preferably a metal label, and most preferably colloidal gold.

A second immobilized ligand corresponding to the analyte of interest is coupled to the analyte test strip at the test zone. First complex and unbound labeled ligand mix with the test sample and be carried along therewith by capillary action (wicking) through the test zone. Analyte sample passes through the analyte test strip bringing the first complexes, if any, into contact with the unlabeled ligand immobilized in the test zone to form a second complex of labeled ligand-analyte-immobilized ligand. The first immobilized ligand is immobilized in the test zone by means known in the art, including covalent bonding or attachment to an insoluble protein-coated surface (see, e.g., U.S. Pat. Nos. 4,200,690 and 5,075,078). When the second complex is formed, a visible color pattern appears in the test zone. Labeled ligand not bound to analyte in the test sample continue migration by wicking into the control zone to contact the ligand immobilized there. The labeled ligand can bind the immobilized ligand in the control zone to form a third complex, and thus be captured in the control zone.

Within the scope of this invention, the labeled ligand forming the complex in the control zone may be the same as the tracer forming the first and second complexes, or it may be a different labeled ligand. The ligand immobilized in the control zone should have specific affinity for the labeled ligand intended to form the third complex. Formation of the third complex is indicated by a visible pattern in the control zone.

Besides sandwich immunoassay method, other assay methods may be implemented in the devices of the invention These methods may include competition and inhibition assays. In a competition assay, the analyte and tracer have similar affinity properties and compete for binding with immobilized ligand. Thus, in absence of analyte, the pattern (e.g., band) in the test zone is of maximum intensity. When present, the analyte binds to immobilized ligand to prevent the tracer from getting captured in the test zone. Thus, the intensity of the test band is reduced, depending on the concentration of analyte in the test sample.

In an inhibition assay, the analyte and immobilized ligand in the test zone each have affinity for the tracer. In the absence of analyte in the analyte sample, the tracer is captured by immobilized ligand, and a visible pattern forms in the test zone. When present, the analyte binds the tracer, thereby preventing it from binding to the immobilized ligand in the test zone. The resulting intensity of the test band is reduced depending on the concentration of analyte in the test sample.

B. Assay System of the Invention

Referring now to FIG. 1 the assay strip of the present invention 101 consists principally of a rigid non-pervious strip, preferably made out of ABS, polycarbonate or similar plastic, 102, which serves as a support for all functional components of the test strip as further described and as a barrier to passage of fluid out of the test strip. Each test strip is typically constructed of a porous membrane 103, which is substantially inert with respect to the analyte, such as urine, and must be porous to allow for capillary flow through the strip. Porous materials, which can be employed, are known in the art and are preferably made from such products as microporous nitrocellulose, cellulose acetate and other cellulose derivatives. The test strip is usually affixed to the support by means of a double-sided tape. The test strip will contain a test zone for binding an analyte 104 to show the presence or absence of an analyte, and a control zone 105 for binding the tracer to indicate the correct operation of the device. The specific binders used for each analyte are well known in the art. Preferably, the test zones and control zones of each analyte test strip lie in the same location on each analyte test strip so each can be viewed in side-by-side fashion. A sample loading zone 106 made of a porous membrane such as a woven or nonwoven fiberglass mat will comprise the upstream end of each analyte test strip. The sample loading pad preferably also has deposited on it the labeled antibody 107, which is taken up by the sample stream and reacts with either the analyte or the binders in the test and/or control zone. The test strip further contains a bibulous sink 108 to absorb the test sample after having passed through the microporous membrane 102. In addition the sample loading zone, the test strips contains a cover 110 for the sample loading zone which extends the length of the sample loading zone and if made of sufficient length can be attached to the underside of the support by means of an adhesive. The cover is made of an impervious plastic film such as polyethylene or polypropylene and tightly adheres to the porous material of the sample-loading zone.

The labeled antibodies are prepared according to the means known in the art. For purposes of producing a clearly visible reaction, labels of metal-containing sols are preferred, with labels of colloidal gold or selenium being most preferred. An example of a suitable product is colloidal gold available from Janssen Life Sciences Products. These colloidal metals produce distinctive visual patterns without addition of further reagents; however, fluorescers (such as fluorescein) and enzymes (such as those identified in U.S. Pat. No. 4,275,149), may also be used.

Selections and choices for test binders (e.g., immobilized antigens, antibodies and other test and control binders), as well as suitable means for their attachment to porous analyte test strip membranes, are well-known to those of ordinary skill in the art and will not be stated in detail here. To maximize contact of test sample with the tracer and all test binders, the area occupied by each reagent on the analyte test strip preferably extends from one side of the membrane to the other.

For further review concerning analyte test strip construction, including selection and preparation of test reagents, the following references provide a representative sample of analyte test strip designs known in the art: U.S. Pat. No. 5,384,264 (commonly owned); U.S. Pat. Nos. 4,491,645; 4,943,522; 5,252,496; 5,714,389 and 5,602,040, the disclosures of which are incorporated for purposes of reference.

Specific examples of test means (e.g., reagents reactive with adulterating components) for use in determining specific values, which reflect the integrity of urine samples, are noted below. In view of the creativity which often accompanies efforts toward adulteration of samples for drug assays, new reagent sets are frequently developed for use in assaying for the presence of such adulterants as they come into use. Thus, those particular test means described herein should be regarded as merely representative of test means which could be utilized in the invention Those of ordinary skill in the art will be familiar with, or can readily ascertain, the identity of other means for use in determining the integrity of urine and other fluid samples.

In each case, however, the test means provide a detectable signal, preferably a visually detectable signal, indicative of adulteration, or the absence thereof, in the analyte sample fluid. In general, such detectable signal will be provided by interaction (e.g., binding) between determinants incorporated in integrity determinant pad 300 (so as to be detectable from surface 300A thereof) and specific adulterants present in the analyte sample fluid.

Figure 2:
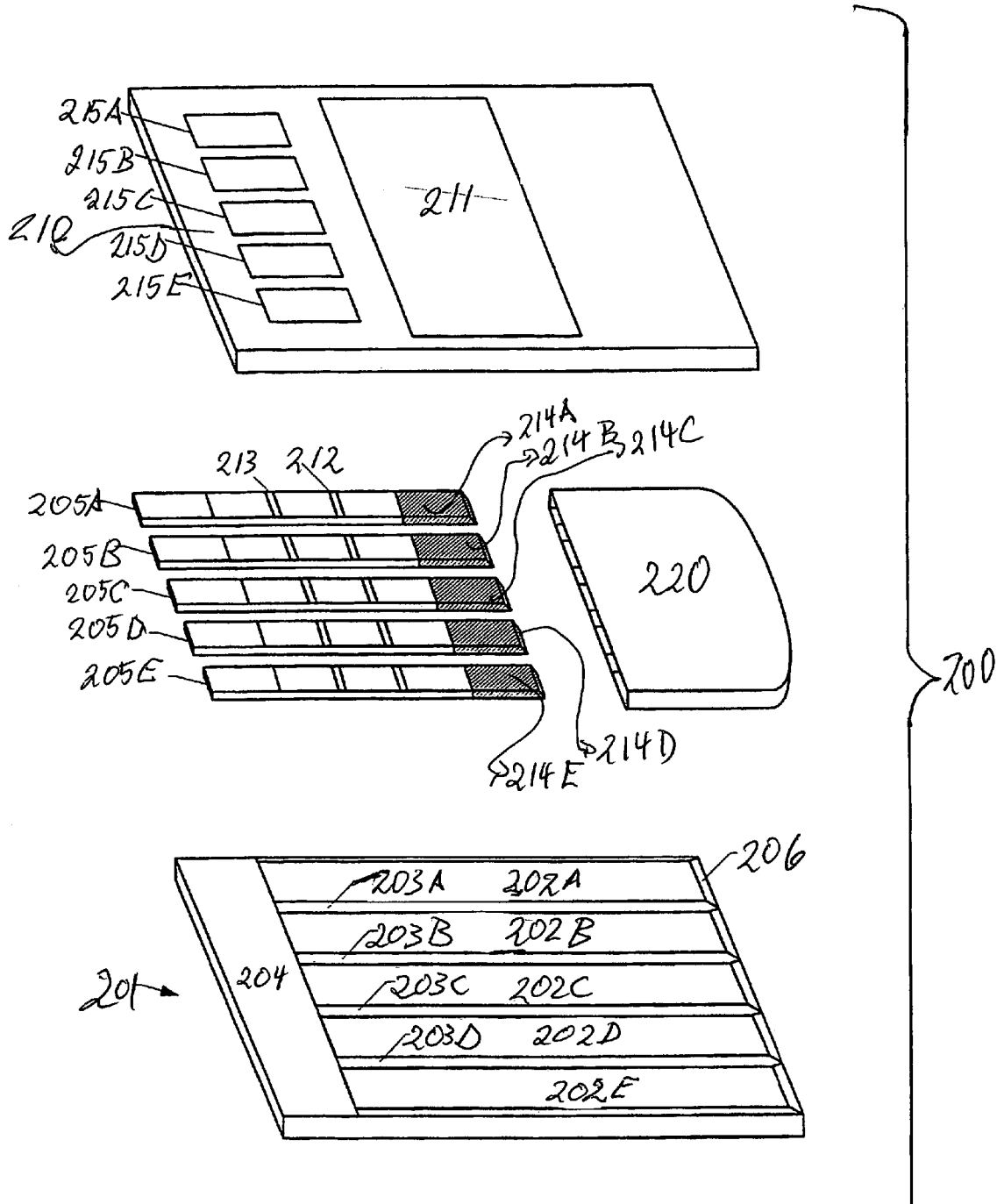
FIG. 2 is an exploded view of the main elements of the assay device of the present invention.

Turning to FIG. 2, a dipstick form of the assay device is shown in exploded view. The device consists of a housing 200, which is defined by base 201 and cover 210. Base 201 can be constructed of any sterilizable material, such as a nonporous plastic (e. g., the commercially available plastic "ABS" supplied by the Monsanto Company of St. Louis, Mo.). Base 201 having a closed end 204 and an open end 206, slots 202A, 202B, 202C, 202D and 202E separated by rails 203A, 203B, 203C and 203D for insertion of test strips 205A, 205B, 205C, 205D and 205E, which are of the construction shown in FIG. 1. A particular advantage of this embodiment of the assay device is its customizability in that test strips specific for different analytes of interest to the user may be inserted into base 201 and that the number of test strips employed may vary (e. g., base 201 may have any number of slots from two upward to accommodate as many test strips as the user may desire). The cover over the exposed strip and sample loading zone of each strip is shown as 214.

Figure 3:
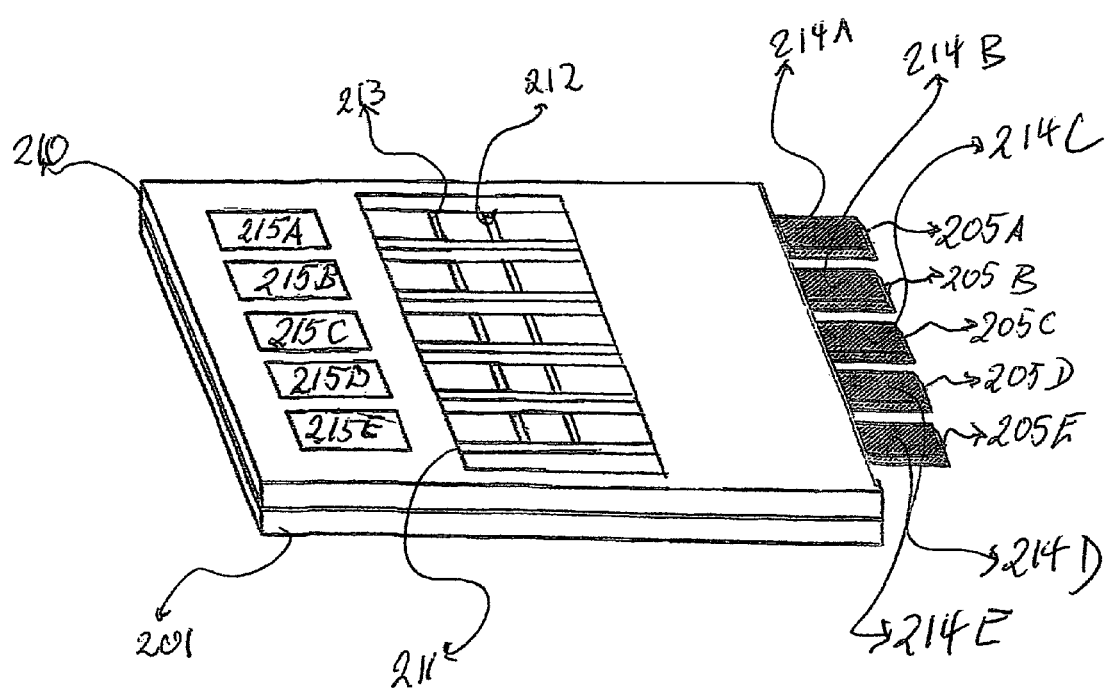
FIG. 3 is a top view of a dipstick assay device of the invention.

Referring also to FIG. 3, when inserted into slots 202A, 202B, 202C, 202D and 202E, the test strips extend out of base 201 beyond open end 206. The length to which the test strips protrude from base 201 must be sufficient to allow the test strips to contact a fluid analyte sample, preferably by immersion, and most preferably without allowing the fluid to contact housing 200. The individual test strips are covered by a plastic strip 214A, 214B, 214C, 214D, and 214E as shown in FIG. 1. Each test strip will have a sample loading pad (not shown) between the rigid support and the cover, a test zone 212 for binding of analyte (to indicate a positive test result for the presence of analyte in the analyte sample) and a control zone 213 for binding of tracer (to indicate correct operation of the assay) located in such a way as to be visible through window 211. Preferably, the test zones and control zones of each test strip lie in the same location on each test strip so each can be viewed in side-by-side fashion. Conveniently the cover is also provided with windows 215A, 215B, 215C, 215D and 215E, which allows the identification of particular test strips used by the labels placed on such test strips.

Selections and choices for test binders (e. g., immobilized antigens, antibodies and other test and control binders), as well as suitable means for their attachment to porous test strip membranes, are well known to those of ordinary skill in the art and will not be stated in detail here. To maximize contact of test sample with the tracer and all test binders, the area occupied by each reagent on the test strip preferably extends from one side of the membrane to the other.

For further review concerning test strip construction, including selection and preparation of test reagents, the following references provide a representative sample of test strip designs known in the art: U.S. Pat. No. 5,384,264 (commonly owned); U.S. Pat. Nos. 4,491,645; 4,943,522; 5,252,496; 5,714,389 and 5,602,040, the disclosures of which are incorporated for purposes of reference.

Test strips 205A, 205B, 205C, 205D and 205E may be secured within slots 202A, 202B, 202C, 202D and 202E by adhesion to the floor of each slot; however, the placement of cover 210 onto base 201 is sufficient to retain the test strips within the base slots without such adhesive. To this end, cover 210 is conveniently constructed of an opaque tape or sheet having at least one transparent window 211 formed therein for viewing of test results along test zone 212 and control zone 213. To secure cover 210 onto base 201, as well as to secure test strips 205A, 205B, 205C, 205D and 205E within slots 202A, 202B, 202C, 202D and 202E, cover 210 is pressed into place to form an adhesive attachment between cover 210 and the upper edges of rails 203A, 203B, 203C, and 203D and end 204.

Conveniently, cover 210 is also provided with transparent windows 215A, 215B, 215C, 215D and 215E through which labels on test strips 205A, 202B, 202C, 202D and 202E can be viewed. The labels (not shown) may be printed with information of use in performing the assay, such as the identity of analyte detectible with each test strip.

In certain instances, it may be desirable to store the assay device after test results are obtained for later viewing. To that end, a five-sided cap 220 is provided for insertion over open end 206 of base 201 (with cover 210 in place) to further protect the protruding ends of test strips 202A, 202B, 202C, 202D and 202E from contact with other materials, from desiccation and from contact with the assay operator. Cap 220 is easily secured onto the assay device by a close fit, such as a friction fit or snap-fit.

EXAMPLE 1

Assay for Six Drugs of Abuse

Six chromatographic strips for detecting drugs of abuse (methamphetamine, opiates/morphine, marijuana/tetrahydrocannabinol, amphetamine, cocaine/benzoylecgonine, benzodiazepine) each of a size of 5 mm.times.73 mm were placed in slots of the device of the invention as shown in FIG. 2. Each strip consisted of a colloidal gold-labeled antibody (specific to the target drug) incorporated into the upstream end of the strip (tracer zone) in the middle of a 30 mm fiberglass matrix, and an antigen-BSA binder immobilized in the center (binder zone) of a 22 mm nitrocellulose membrane lying downstream of, and in fluid communication with, the fiberglass matrix (wherein the antigen is either the drug of interest or an analog thereof having the same immunogenicity). The nitrocellulose membrane was adhered to a rigid strip of vinyl plastic as support and as a barrier. A strip vinyl film covered the fiberglass matrix and was attached to the underside of the rigid plastic support Downstream to the nitrocellulose membrane was a 26 mm long filter paper. The matrix, membrane and filter paper were attached to the vinyl sheet so each was in fluid communication, by overlapping 2 mm of each of their ends.

The device was immersed in to sample of urine and the results were read after 10 minutes. The presence or absence of a pink-rose color band in the binder zone indicated negative or positive results for the presence of each drug of interest in the analyte sample.

For comparison, additional aliquots of the analyte samples were separately tested for the presence of the same drugs of abuse by a commercial assay (Syva EMIT EIA II). The second panel of test results correlated with the results obtained according to the invention.

Although the invention has been described with reference to the presently preferred embodiment, it should be understood that various modifications can be made without departing from the spirit of the invention. Accordingly, the invention is limited only by the following claims.

The invention claimed is:

1. A device for assaying a fluid for the presence or absence of analytes comprising:
    (A) a base having adjacent slots therein of sufficient length for insertion of a test strip therein, wherein each slot is defined by (a) a floor, (b) raised walls depending upwardly from the floor to separate each adjacent slot from the next, and (c) at least one open end;
    (B) a multiplicity of test strips each test strip comprising microporous membrane on a rigid backing having a test zone for a binder for a specific analyte and a control zone thereon and having an upstream and a downstream end, said upstream end comprising a sample absorbing porous pad attached to said rigid backing and in fluid contact with said membrane, said downstream end containing a second porous pad to absorb tested sample,
    (C) a first cover attached to the upward most surface of each raised wall of the slots of the base and coextensive with said base, wherein the cover retains the test strips within the slots and has a first transparent window formed therein through which the test zone and the control zone of each of the test strips can be viewed,
    (D) wherein a each test strip is inserted into a different slot of the base so the upstream end and sample absorbing pad of each test strip protrudes out of the open end formed by said base and said first cover, and wherein each protruding test strip part is freestanding and not in contact with any other test strip; and wherein the flat surface of the protruding sample absorbing pad is covered by a second separate cover, and
    (E) a third cover in the form of a removable cup covering the freestanding protruding ends of the test strips and said second cover.

2. The device according to claim 1 further comprising a second transparent window formed within the first cover through which the strips can be viewed and identified.

3. The device according to claim 1 wherein each test strip has a test zone therein and each test zone contains a binder specific for a different analyte.

4. The device according to claim 3 wherein each binder is specific for a different drug of abuse.

5. The device according to claim 1 wherein each test strip further comprises a label downstream of the of the test zone, which label identifies the analyte for which the binder is specific.

6. The device according to claim 5, wherein the label on the test strip is visible through the second transparent window.

* * * * *